(12) United States Patent
Turri

(10) Patent No.: US 7,402,040 B2
(45) Date of Patent: Jul. 22, 2008

(54) OSSEOUS PREPARATION TOOL USED IN DENTAL MEDICINE AND DEVICE FOR THE USE THEREOF

(75) Inventor: Achille Turri, Morbio Inferiore (CH)

(73) Assignee: Arsline SA, Vacallo (CH)

( * ) Notice: Subject to any disclaimer, the term of this patent is extended or adjusted under 35 U.S.C. 154(b) by 596 days.

(21) Appl. No.: 10/505,865

(22) PCT Filed: Feb. 27, 2003

(86) PCT No.: PCT/CH03/00145

§ 371 (c)(1),
(2), (4) Date: Aug. 27, 2004

(87) PCT Pub. No.: WO03/071978

PCT Pub. Date: Sep. 4, 2003

(65) Prior Publication Data

US 2005/0118550 A1    Jun. 2, 2005

(30) Foreign Application Priority Data

Feb. 27, 2002    (CH) .................................... 0340/02

(51) Int. Cl.
*A61C 3/02* (2006.01)
*A61B 17/00* (2006.01)

(52) U.S. Cl. .......................................... 433/165; 606/80

(58) Field of Classification Search .................. 433/165
See application file for complete search history.

(56) References Cited

U.S. PATENT DOCUMENTS

| 5,261,818 | A | * | 11/1993 | Shaw | 433/165 |
| 5,437,675 | A | | 8/1995 | Wilson | |
| 5,453,008 | A | * | 9/1995 | Berlin | 433/122 |
| 6,171,312 | B1 | | 1/2001 | Beaty | |
| 6,364,662 | B1 | * | 4/2002 | Kumar | 433/165 |

FOREIGN PATENT DOCUMENTS

| CH | 410 276 | 3/1966 |
| DE | 43 16 955 | 5/1994 |
| DE | 197 32 983 | 2/1999 |
| WO | 01/85051 | 11/2001 |

* cited by examiner

*Primary Examiner*—Cris Rodriguez
*Assistant Examiner*—Candice C Stokes
(74) *Attorney, Agent, or Firm*—Young & Thompson

(57) ABSTRACT

The active portion of an osseous compression tool for use particularly in dentistry for the preparation of an osseous seat has a cross-section whose perimeter, e.g. of polygonal shape, is defined such that a rotational actuation of the tool around its axis, at least in one direction, preceded or accompanied by its actuation in an axial direction inside the seat, has the effect that the osseous matter is compressed and that the seat is imparted a perimeter of a predetermined shape. In a variant embodiment, a rotation of the tool in the opposite direction allows a scraping or cutting of osseous matter. A tool holder includes a percussion system and allows the translational and rotational actuation of the tool manually or automatically.

37 Claims, 10 Drawing Sheets

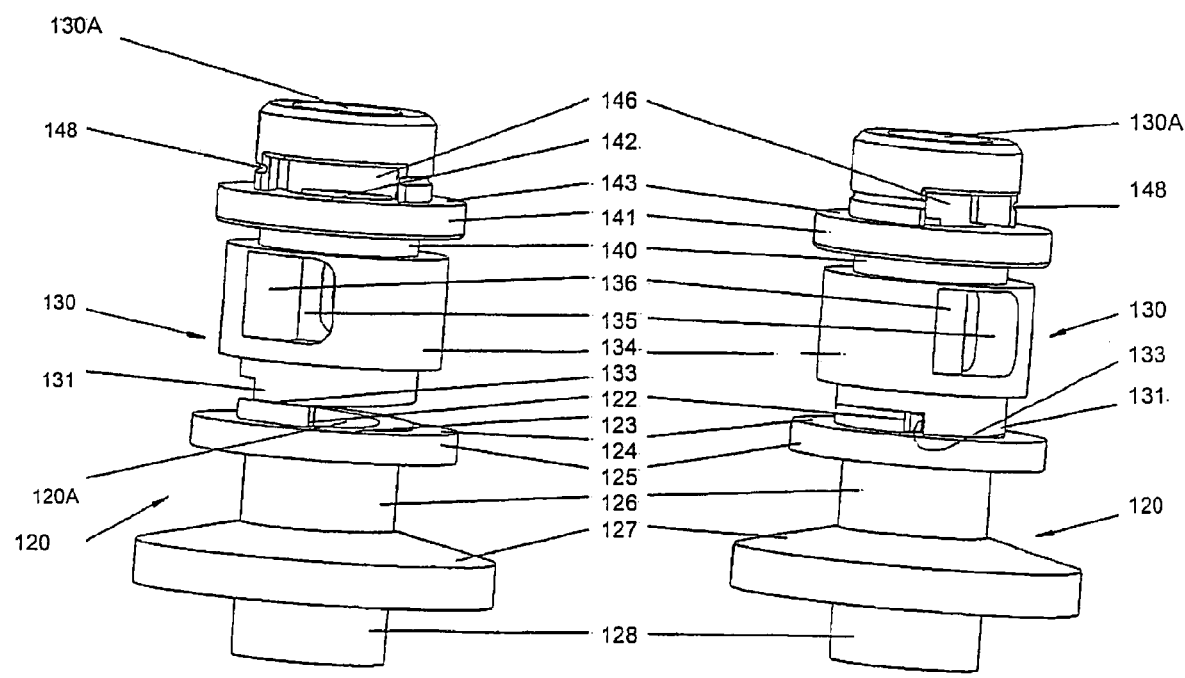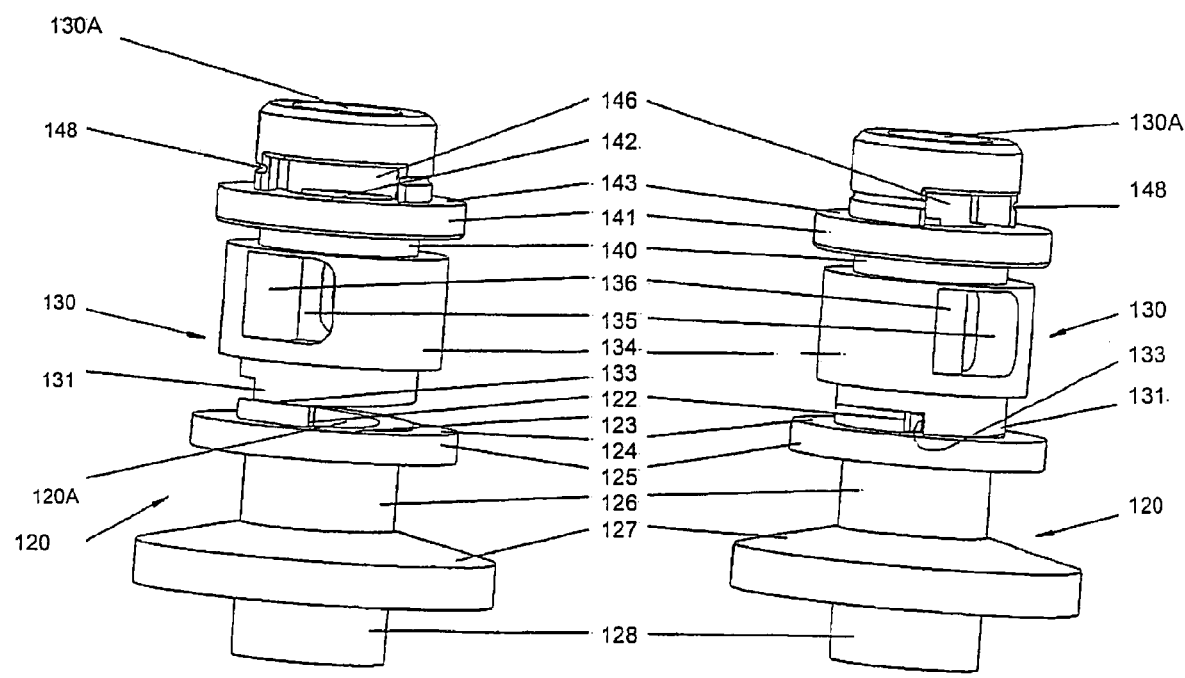

Figure 1A:
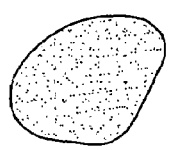
Figure 1B:
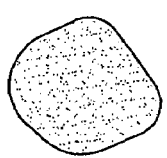
Figure 1C:
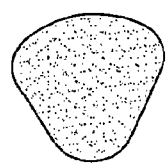
Figure 1D:
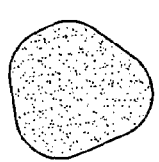
Figure 1E:
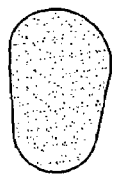

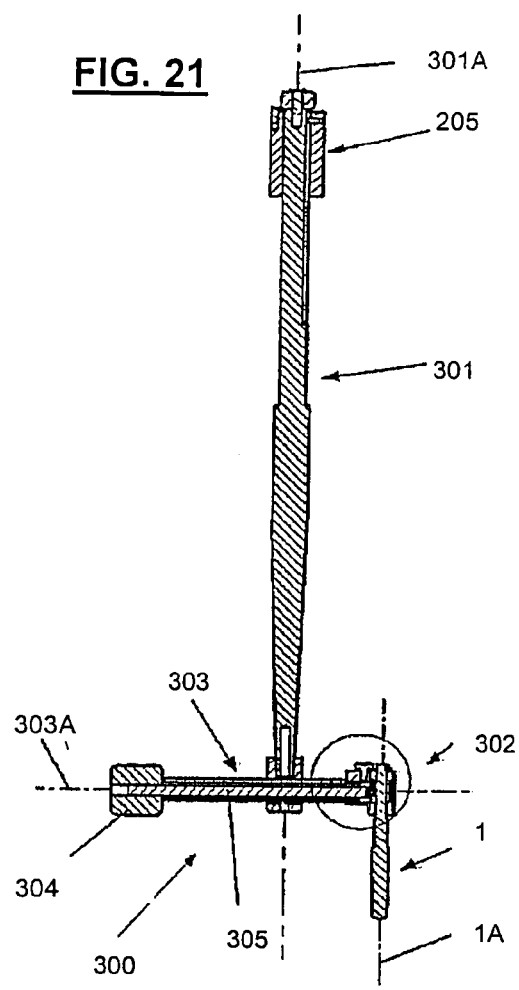
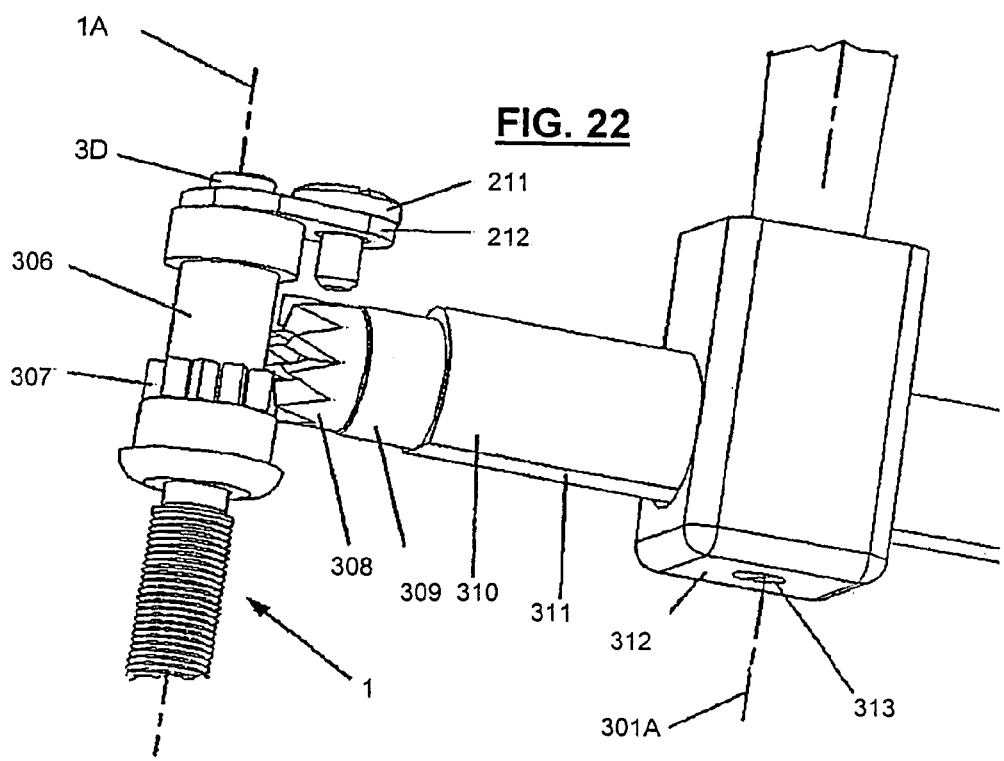

OSSEOUS PREPARATION TOOL USED IN DENTAL MEDICINE AND DEVICE FOR THE USE THEREOF

The present invention relates to an osseous preparation tool, particularly a dilator for use notably in dentistry according to the preamble of independent claims 1 and 2, and to a device allowing the operation of a tool of this type.

The preparatory work prior to the placement of an axially inserted implant in a patient includes the preparation of an osseous site (or seat, also called implant seat or implant bed) by the specialized practitioner in the jaw of the patient. To this end, a hole is produced in the jaw, whose diameter may vary and is generally in the order of 3 to 6 mm, this hole constituting a kind of artificial alveolus.

At present, there are two methods for preparing osseous sites for the placement of implants: most frequently, by drilling into the jaw bone (i.e. by conventional drilling with bone particle removal), and more infrequently by osseous compression by means of a punch (currently called dilation technique (of the hole), the compression of the osseous matter at the periphery of the hole resulting from the dilation by the punch). From a practical point of view, the preparation of the implant seat may be complicated right from the beginning by a first problem of physiological nature. In fact, in the area intended for the placement of the implant, the osseous matter may be insufficient either with regard to its volume, in the transversal and/or axial dimensions, or to its density, if it consists of a loose spongiosa (trabeculation with large lacunae). Especially in the second mentioned situation, the drilling technique is often inappropriate since the removal of osseous particles may result in an insufficiency of the osseous structure and hence in a deficient mechanical retention and thus compromise the primary stability of the implant. However, besides a high mechanical resistance of the implant, this stability is a strictly necessary condition for the physiological osteo-integration of the implant.

This is why certain practitioners, when confronted with this situation, currently apply a method of osseous preparation that consists of dilating the site by compression of the surrounding bone tissue, thereby making it more compact, more resistant mechanically, and capable of a better osteo-integration, by means of cylindrical or slightly conical punches. To this end, possibly after having drilled a starting hole of a small diameter (of the order of 2 mm) by means of a usual bur (pilot bore), the practitioner will insert a first punch whose diameter is slightly greater than the diameter of the bur and strike the punch by means of a hammer with a force that may be quite considerable until the desired depth is attained, and subsequently perform the same operation with a second punch whose diameter is slightly greater than that of the preceding punch, and so forth, while using a set of punches of increasing diameter to obtain the hole of the desired diameter (and depth).

Of course, the drilling technique and the osseous compression technique do not necessarily exclude each other but may on the contrary appear to be complementary during the preparation of one and the same osseous site. In fact, rather than preparing an implant bed entirely with punches, it may appear to be preferable or even compulsory, in view of the hardness of the bone and/or of a possible variation of that hardness in the course of an operation, to drill several progressive bores (e.g. up to 3.20 mm) at first, followed in a second phase by at least one dilating operation using one or a plurality of punches until the final diameter (e.g. 3.50 mm) is attained.

The bone compression technique by means of the currently used punches suffers from a series of several drawbacks:

The use of such tools is highly traumatic for the patient. Indeed, since the anesthesia is local, the patient will not really feel any pain but nevertheless perceive the resonance of the blows in his or her head.

Since the resistance and the consistence of the bone cannot be sensed with sufficient precision, it is very difficult for the practitioner to appreciate these parameters and thus to adjust the extent of the dilation in order to optimize the retention of the implant and its primary stability. Neither is it possible to counteract the tendency of the punch to deviate from the correct working axis, a drawback that will become apparent in the case of an osseous cortex having an asymmetrical thickness in the transversal direction, which is frequently the case, e.g. in the area of the superior incisors and canines where the palatal cortex is typically thicker.

Besides the fact that the intensity of the blows caused by the strokes of the hammer on the punch is difficult to control, it is necessarily variable. Moreover, since the practitioner is unable to adjust the compression of the osseous matter toward the periphery of the hole to the anatomical parameters of the moment with sufficient precision, he is also unable to calibrate the hole correctly. However, a perfect calibration is an indispensable condition for an optimal primary stability, which in turn is an obligatory prerequisite for the best possible osteo-integration in a given patient.

In addition to these drawbacks, the possible inhomogeneity of the osseous density or hardness (mentioned above) along the wall of the hole may require the temporary use of a conventional cutting bur.

Figure 1F:
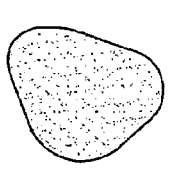
Figure 1G:
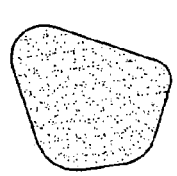
Figure 1H:
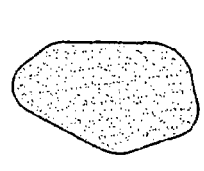

Moreover, conventionally, the cross-section of holes made in situations of insufficient osseous density by means of punches of the prior art is necessarily circular as these tools are cylindrical or at best conical. But on the other hand, the root seats of the natural teeth (particularly the portions at the base of the crown (or at the neck) have different shapes, i.e. irregular contours or boundaries that deviate more or less significantly from the circular shape, as shown schematically by way of examples in FIG. 1A (upper central incisor), 1B (lower canine), 1C (upper canine), 1D (lower canine), 1E (first upper premolar), 1F (second lower premolar), 1G (first upper molar), 1H (first lower molar). It appears that a circular osseous seat may be found to be quite satisfactory or even indicated for the placement of certain implants (see e.g. FIG. 1F). In contrast, in other cases (see e.g. FIGS. 1A, 1C, 1E, 1H), a hole of circular cross-section represents a stopgap that is all but ideal, while conforming at least approximately to the natural shape would offer the double advantage of a better anchoring and of an ideal esthetic of the prosthetic superstructure.

Moreover, the shape or profile of a root is neither or not necessarily perfectly cylindrical or conical in the axial plane.

Thus, the use and the manipulation of cylindrical punches seem unrefined and little appreciated, and it is easily understood that an optimum result cannot be ensured under these conditions while the encountered disadvantages substantially restrain the limits of implantology when confronted with a situation of insufficient osseous density. Besides, some practitioners are not familiar with their manipulation, and those who are rarely use it as they mostly prefer the conventional drilling technique even when confronted with the aforementioned critical situation, which may lead to clinically inadequate results. However, the problem is all the more critical as the drilling technique has been found to be insufficient or even contraindicated in many situations since especially the osseous densities of the edentulous upper jaw are statistically poor or very poor in 80% of the cases (bone density categories D3 and D4 according to Misch).

DE-A1-197,32,983 discloses a tool for effecting an enlargement, or more precisely a spreading of the segments of an osseous crest (also called osseous green-wood dislocation or Bone-Splitting) that has been cut along its longitudinal axis, to increase the transversal diameter for the placement of an implant. The problem that arises is to avoid an osseous fracture, i.e. the lower part of the two layers (resulting from the spreading) must not separate in any event. To solve this problem, the tool suggested in this disclosure, which applies the principle of operation of an expansion lever, has a cruciform cross-section with a "central peg" (10, 11) with rounded radial ends and, in the axial direction, over a distance, a slightly conical end section with a rounded or stepped axial apical end. For its operation, the tool is inserted into a handle having a bend. The "Bone-Splitting" operation, i.e. the spreading of the segments of the osseous crest, is achieved gradually by means of a set of tools of increasing width (the width of the peg being inferior to that of the tool) that are each subjected to rotational movements of a determined and limited angle of the order of 45°. The disclosed tool offers a solution, inter alia, with regard to the aforementioned insufficiency in volume of the osseous matter, even though it appears upon analysis that the risk of involuntary removal of osseous matter is not entirely excluded. On the other hand, the problem of an insufficient consistence of the osseous matter is not resolved at all, and a compression of the mesh structure of the bone cannot be achieved. This is not the aim, and the issue is not discussed in DE-197,32,983.

The goal of the present invention is twofold, the first part consisting in the provision of a tool for osseous preparation particularly for use in dental implantology that allows performing an actual compression of the alveolar bone structure, whatever differences with regard to hardness, density, and bone structure may appear in the course of the preparation, and that is free from the drawbacks described above.

This first area of the objective is attained by a bone compression tool or dilator implementing the means defined in either one of independent claims 1 and 2, the dependent claims referring to characteristic features of preferred embodiments.

It will be noted in this context that the claimed tool, besides eliminating the discussed drawbacks, offers still other important advantages that will be appreciated hereinafter in reading the detailed description. More particularly, an advantage of functional nature shall be mentioned, namely a better retention of the implant or, in other words, a better mechanical anchorage and the optimization of the latter in all circumstances and conditions including changing circumstances in which the local bone density is reduced, which cannot be achieved with tools of the prior art as the quality of the anchorage essentially depends on the interface between the bone and the implant.

This interface in turn is determined by two parameters.

A first parameter relates to the bone quality, i.e. its density. The tool allows to improve the bone density through compression. By crushing the bone lacunae, both the bone density and the area of contact with the implant are increased. In the present case, besides the fact that the compression is effected with a maximum of comfort for the patient as it is very "gentle", it is adapted to the individual as all specific particulars of the bone structure in the implant site in the patient are best utilized.

The second parameter is determined by the size of the area of contact between the implant and the bone wall of the hole, which is influenced not only by the surface area of the implant and its microscopic structure of greater or lesser roughness, which is common, but also and additionally, with the novel tool of the invention, by the macroscopic shape of the obtained hole. In fact, depending on the shape or the particular embodiment of the tool, it is possible to achieve an implant bed other than circular—which may be advantageous, particularly with regard to the location of the implant and to the anatomical or physiological characteristics of the osseous site—e.g. of an ovoid shape (or according to a Cassini's curve) for a premolar location, where the wall surface is greater than that of a cylindrical wall (of identical base diameter). The contact surface will therefore be increased, or at least less reduced if the depth of the implant must be relatively shallow or limited for some reason.

By a better reproduction or approximation of shapes and proportions of natural alveoli, specific embodiments of the osseous preparation tool allow to achieve placements for implants of ideal dimensions. Thus, the latter are capable of supporting fixed prosthetic superstructures exhibiting substantially better qualities than current fixed prostheses (considering that today the shape of artificial roots is still substantially dissimilar from the different natural roots), both with regard to mechanical aspects (an implant of ovoid shape offers better resistance to torsional forces than an implant of circular shape) and to physiological and esthetic aspects (elimination of recesses or cavities, placement of prosthetic elements (crowns on implants) that are true reproductions of natural teeth).

Consequently, by allowing the elaboration of alveoli of specifically adapted shapes, i.e. similar to natural alveoli, the osseous preparation tool, which is furthermore polyvalent, opens the way for the creation of a new generation of implants whose shapes are anatomical as well.

The second part of the objective is of course closely related to the aforementioned first part and refers to the mode of operation of the dilator or more generally of the osseous penetration tool. Thus, the invention also refers to a novel and original device for said operation which is the object of claim 23. The dependent claims of the latter refer to particular embodiments of the device, which may be either manual or automatic.

Figure 2A:
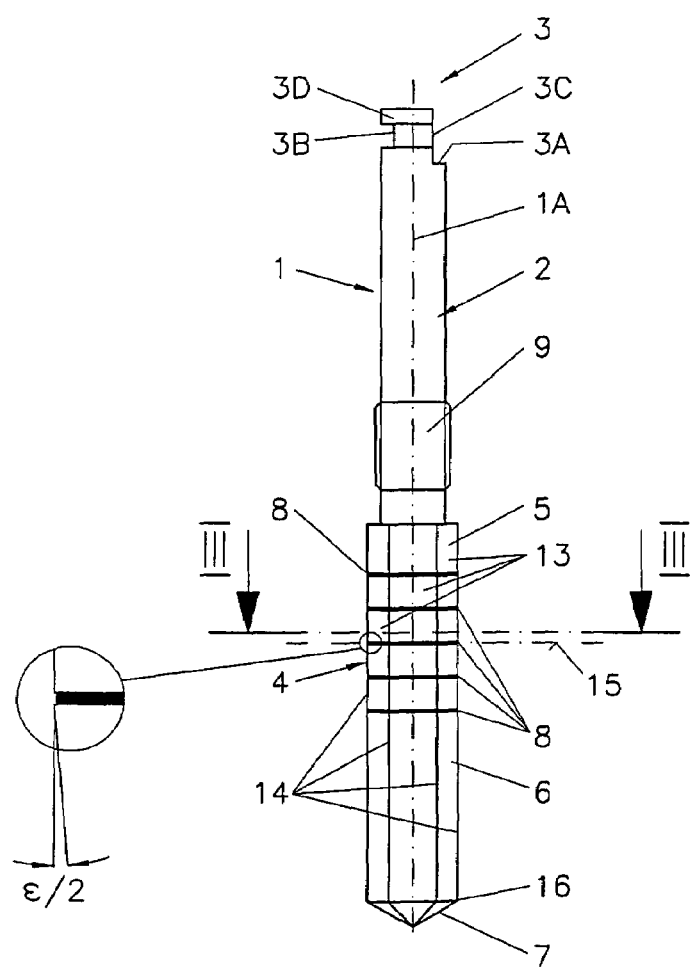
Figure 2B:
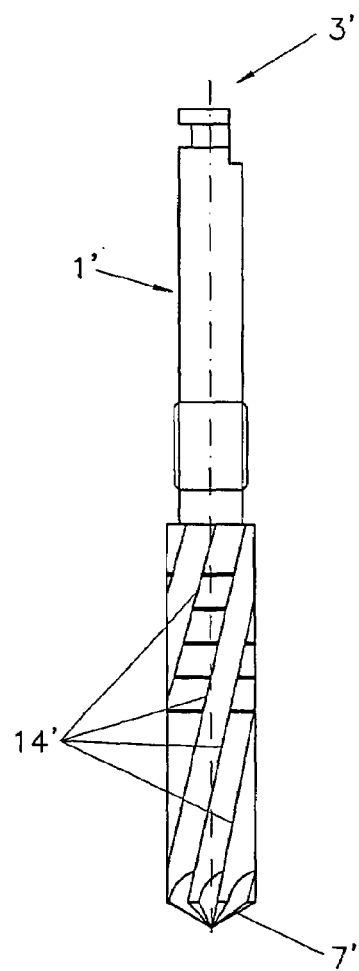
Figure 3:
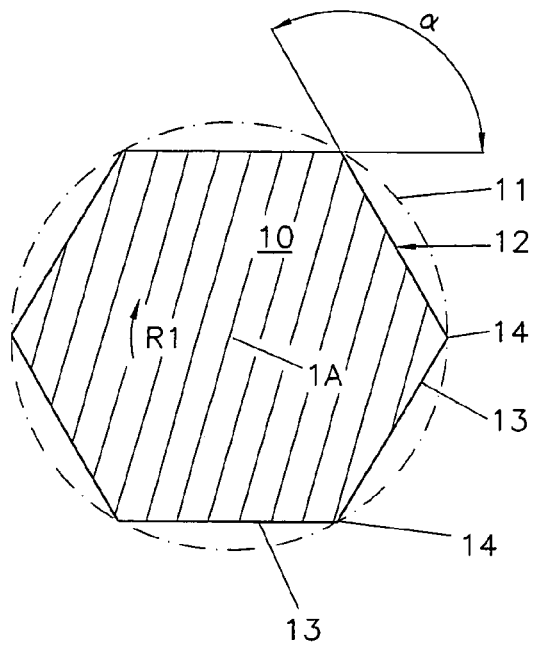
Figure 6:
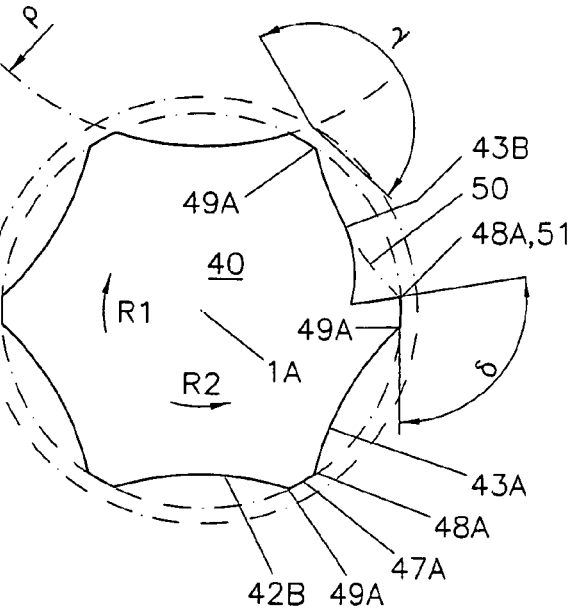
Figure 7:
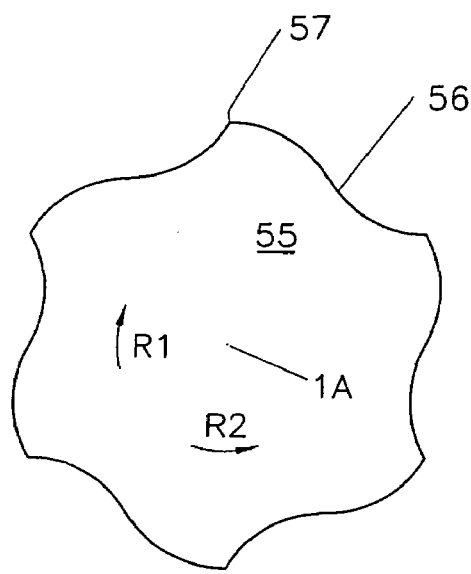
Figure 8:
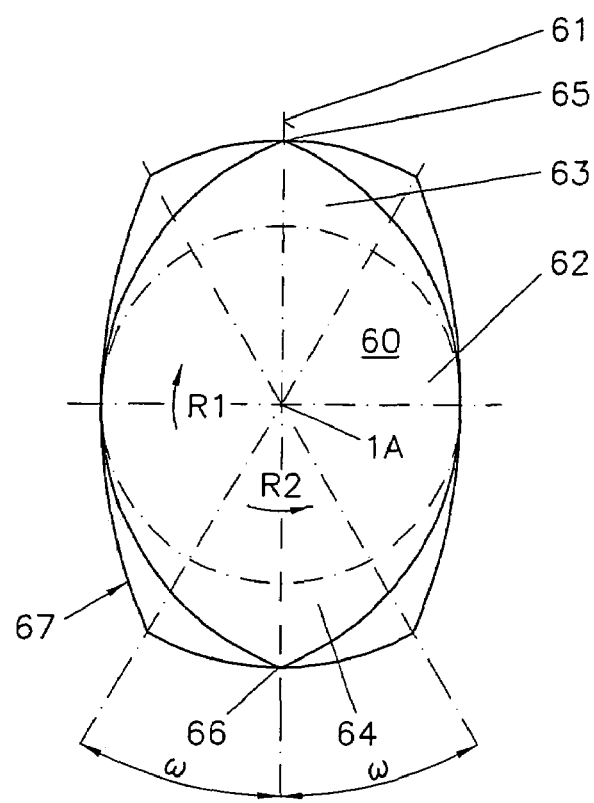
Figure 9A:
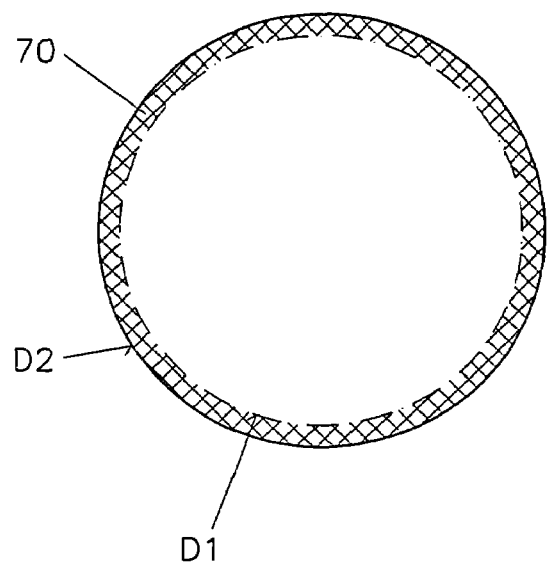
Figure 9B:
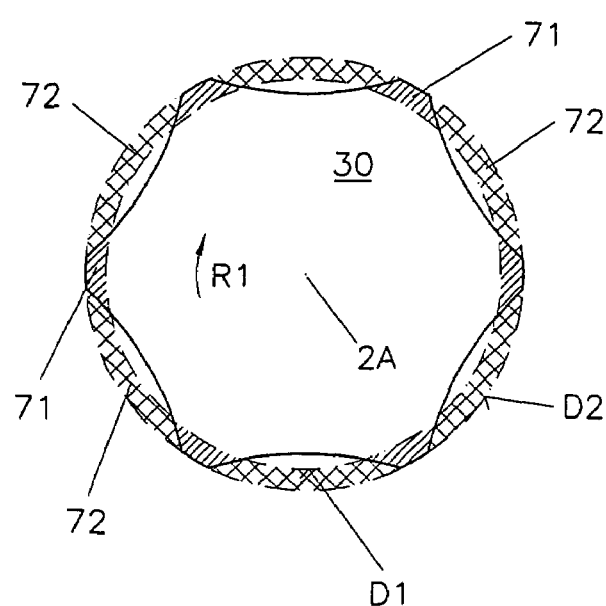
Figure 10:
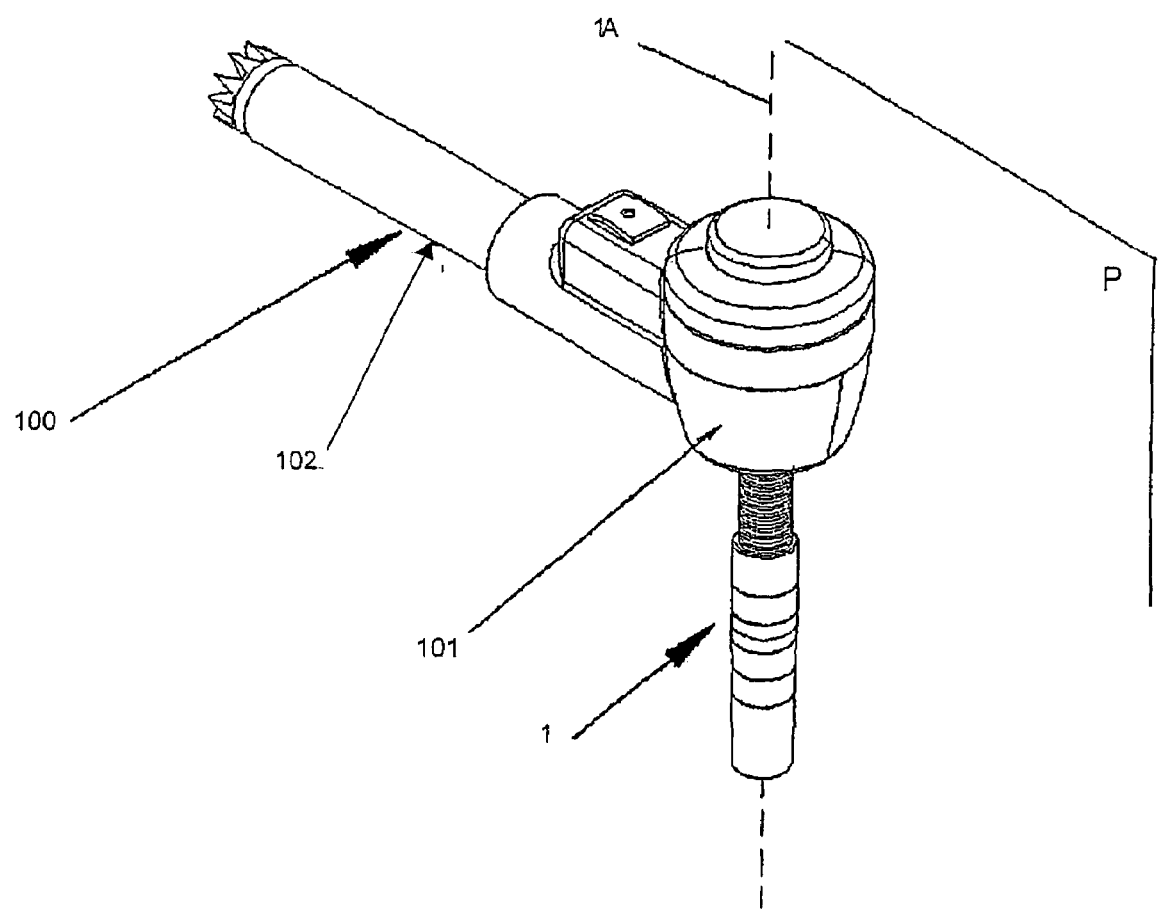
Figure 11:
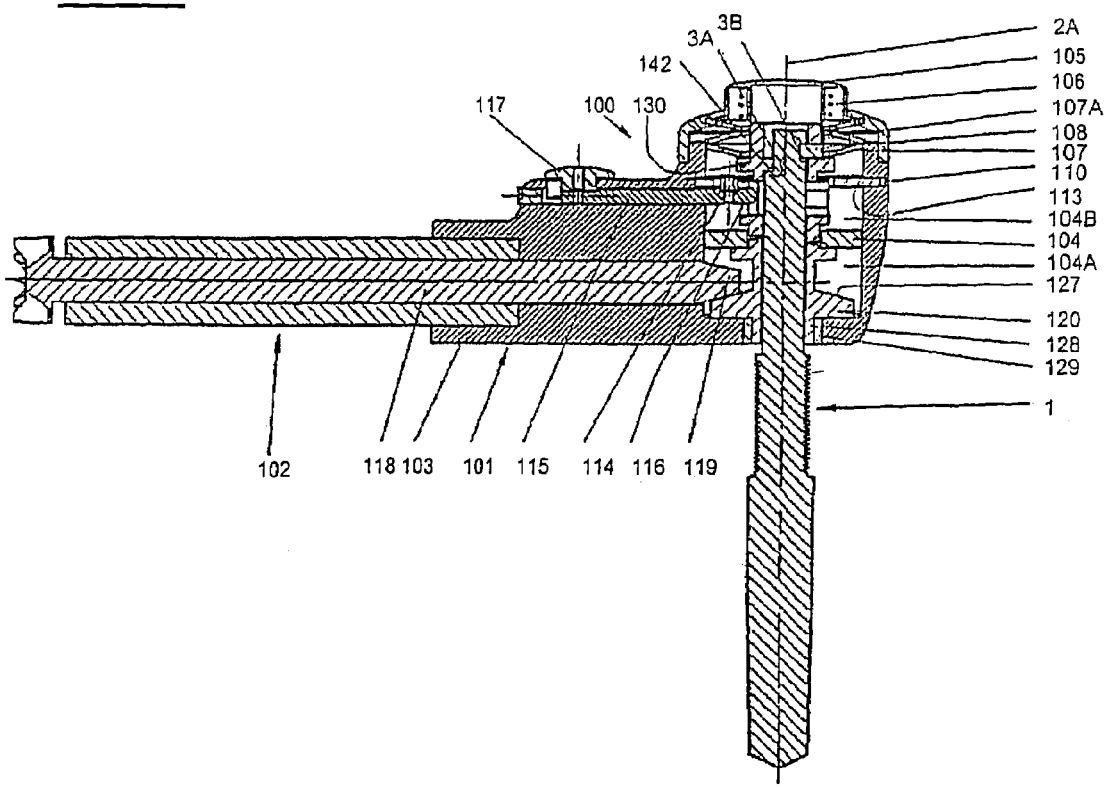
Figure 12:
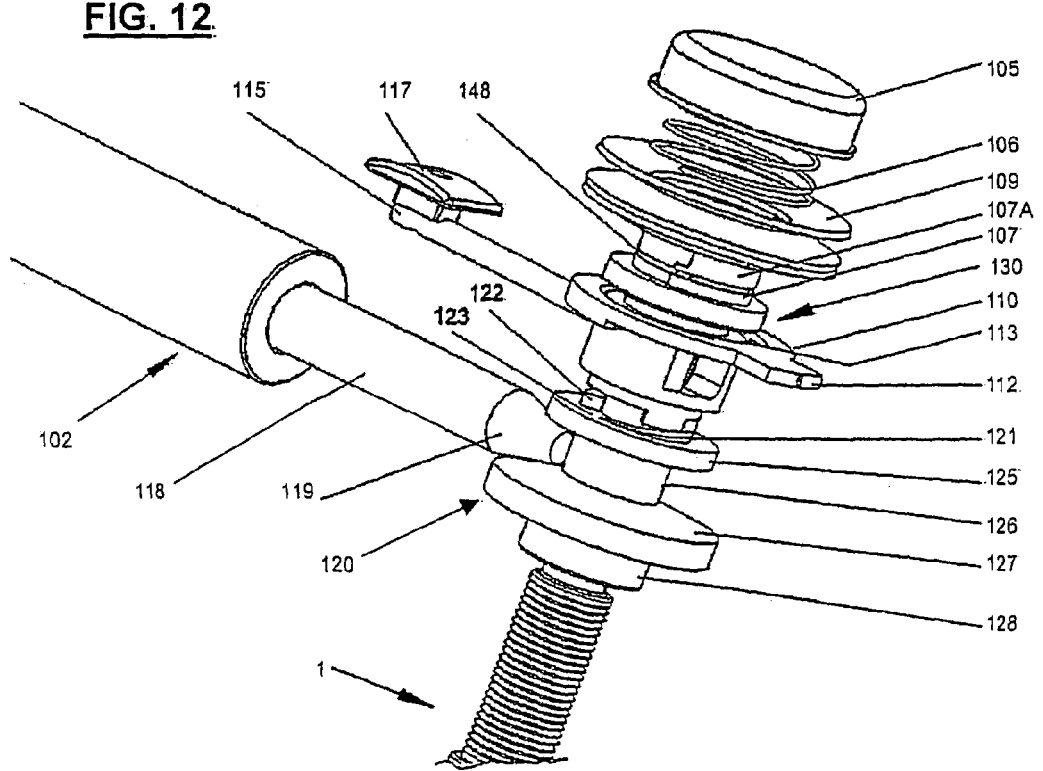
Figure 15:
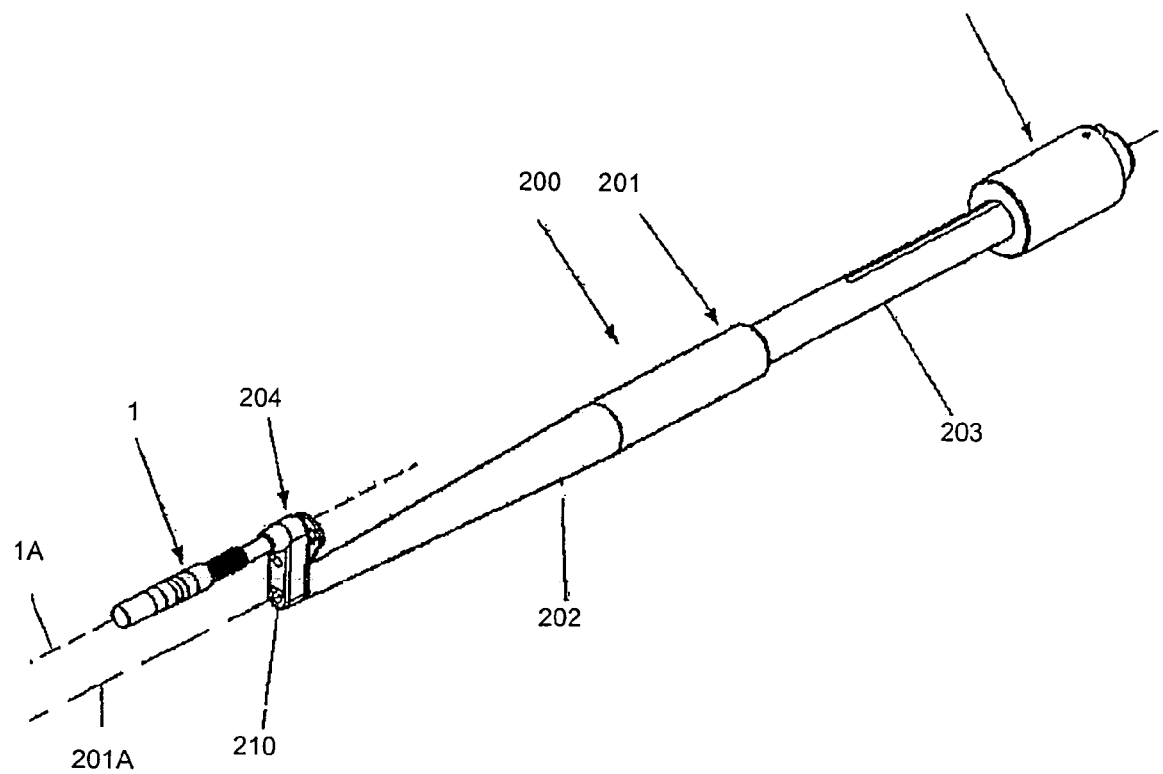
Figure 16:
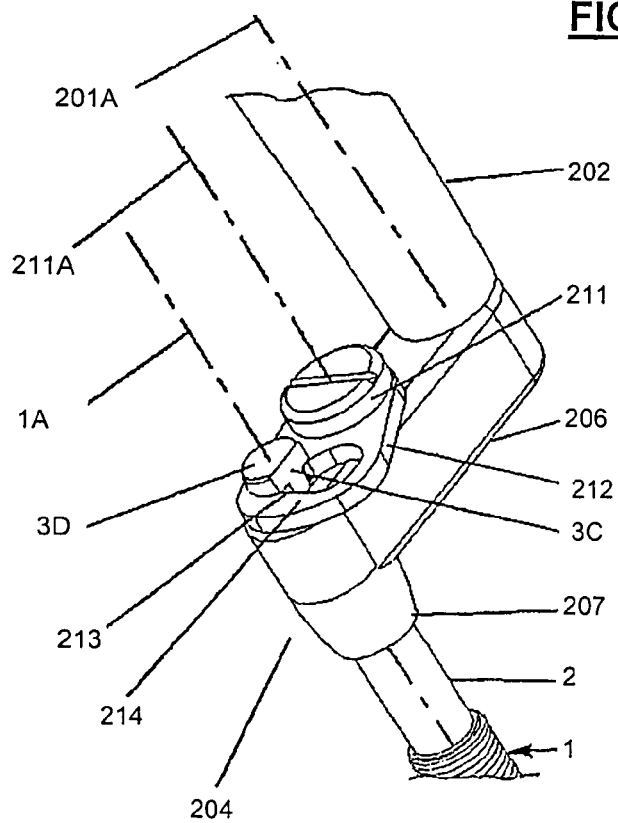
Figure 17:
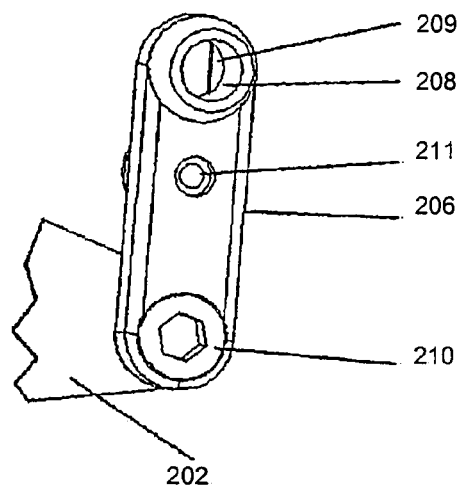
Figure 18:
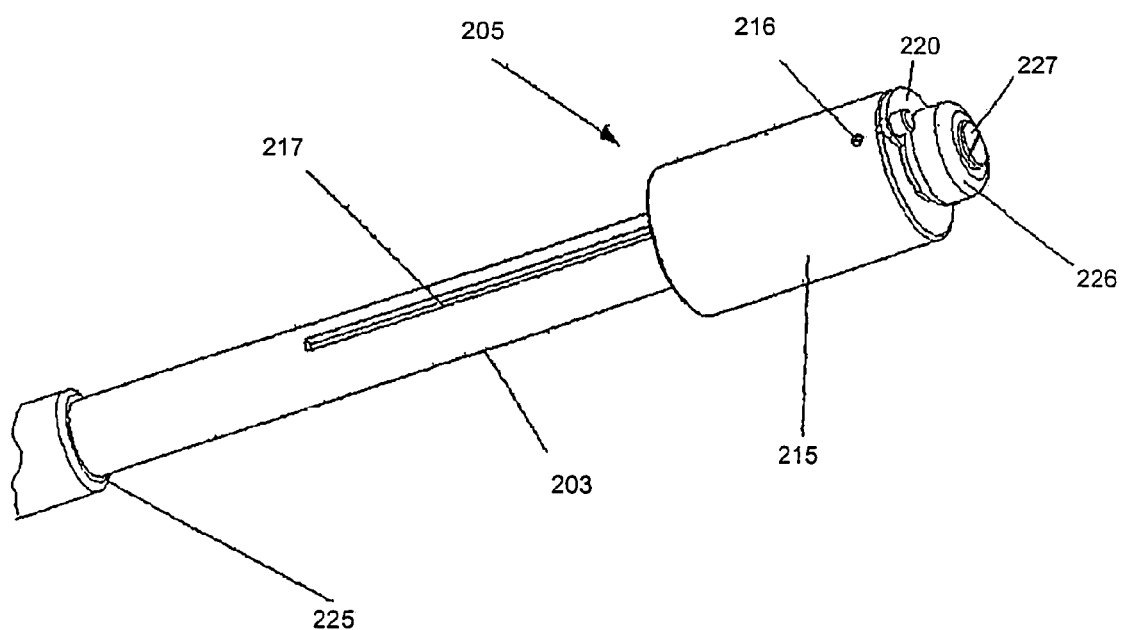
Figure 19:
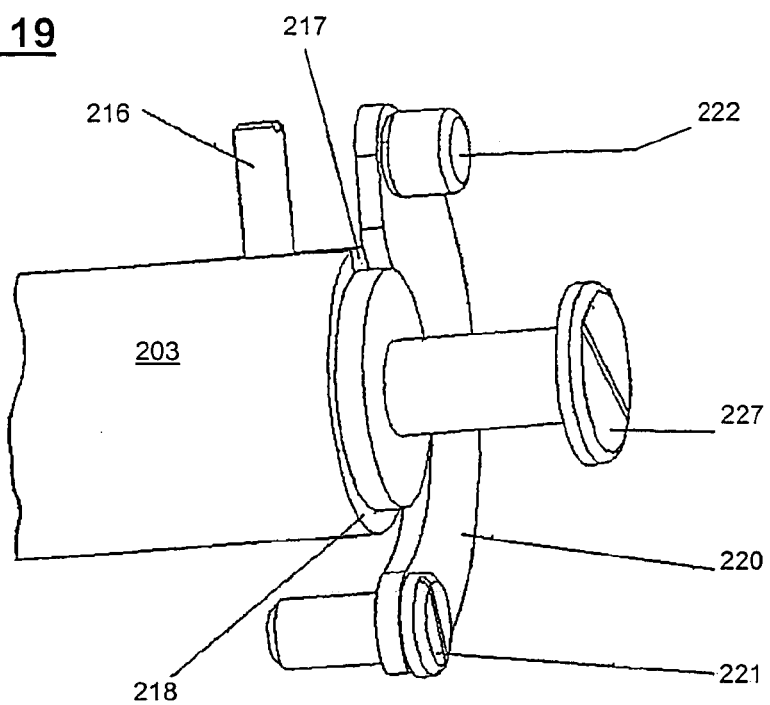
Figure 20:
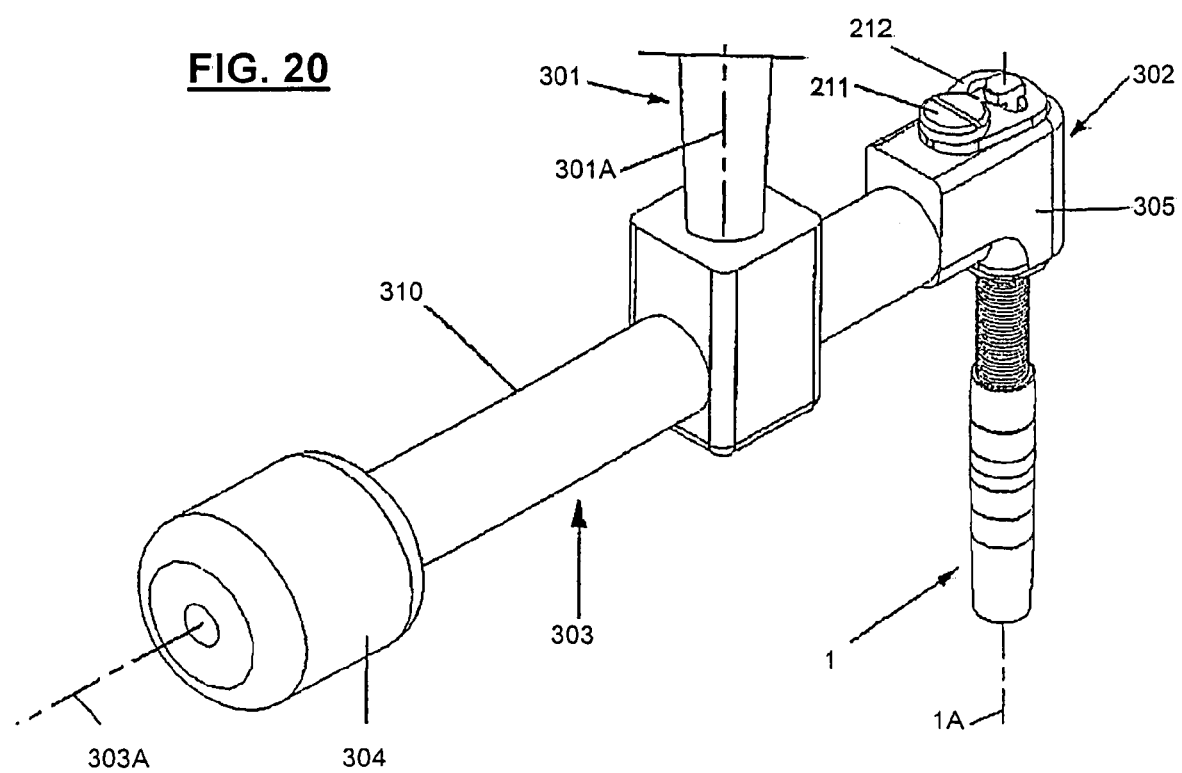

Different embodiments of the dilator and of the device for the manipulation of the latter shall be described hereinafter as non-limiting examples with reference to the enclosed drawings, where FIGS. 1A to 1H (already discussed above) show sectional shapes of teeth roots at the base of the crown (near the neck), FIGS. 2A and 2B show front views (orthogonal axial planes) of an embodiment of the dilator in two variants, FIG. 3 shows a cross-section according to line III-III in FIG. 2, FIGS. 4 to 7 represent variants of a first embodiment of the cross-section of the active part of the dilator, FIG. 8 represents a variant of a second embodiment of the cross-section of the active part of the dilator, FIGS. 9A and 9B are comparative diagrams (conventional punch vs. dilator of the invention), FIG. 10 shows a perspective view of an embodiment of an automatic actuating device of a dilator, FIG. 11 shows a cross-section of this embodiment of the automatic device in a plane (P) of FIG. 10, FIG. 12 shows the assembly of the different elements of the actuating device in a perspective view with the housing removed, FIGS. 13 and 14 show perspective views of the mutual cooperation of two members, the reducer and the striker, with the latter in the lifted and lowered position, respectively, FIG. 15 shows a perspective view of an embodiment of a manual device, FIGS. 16 through 19 show explanatory diagrams of the operation of this embodiment of a manual device, FIG. 20 shows a (partial) perspective view of a further embodiment of a manual device, FIG. 21 shows a sectional view of the device shown in the FIG. 20 in a plane of symmetry, and FIG. 22 shows another (partial) perspective view of this other embodiment of a manual device, while it will be noted that the scales of representation are not uniform in the different figures.

A simple embodiment of a dilator 1 is represented in a front view in FIG. 2A and in a sectional view according to line III-III of the latter in FIG. 3. This dilator, with main axis 1, comprises a stem 2 with a stem shank 3 provided with a shoulder 3A, a groove 3B, a flat 3C and a cap 3D, the stem being followed by an active portion 4 for shaping the hole, i.e. the osseous site or implant site. Portion 4 comprises surfaces 13 that are separated by straight edges 14. According to a variant shown in FIG. 2B, dilator 1' may be provided with helical edges 14'. Active portion 4 is advantageously composed of a rear subsection 5 and a front subsection 6 whose end comprises an apical portion or attack (lead) head 7 (7' in the variant according to FIG. 2B). Subsection 6 extending between a plane 15 and the base 16 of head 7 advantageously exhibits a slight conicity ϵ, e.g. of the order of 1° (see the enlargement of the encircled portion). The conicity offers a double advantage. Actually, in the elaboration of an osseous site, the successive insertion of a set of dilators 1 with radial cross-sections of increasing dimensions occurs very gently since the cross-section of the active portion of a dilator with base 16 is dimensioned such that it is equal to the dimension of the cross-section of the active portion of previously used dilator 1 at the height of plane 15 at the most. Furthermore, it ensures a tighter retention of the implant, i.e. of better quality. In practice, the length of the frustoconical subsection 6 is advantageously of the order of ten millimeters, thereby corresponding to the average depth of osseous sites that are elaborated for the placement of an implant (while it will be noted that the term frustoconical does not mean here that the cross-section of subsection 6, and more generally portion 4, is circular (see below)). Active portion 4 is preferably provided with depth marks 8 while the stem may comprise in its forward portion (seen in the direction from the stem to the active portion) a threaded section 9 intended to cooperate with a safety device (described in WO 00/74585 to the inventor of the present application) that excludes the introduction of the dilator into the hole past a depth limit P as previously determined by the practitioner.

However, as discussed above, even a conical profile in the axial plane of the dilator may not be ideal as it may be too different from the natural and individual profile. Therefore it is possible to provide dilators where the profile of portion 4 or at least of subsection 6 has any other adequate shape. Thus, amongst other examples, a curved profile is conceivable (e.g. having the shape of a flame turned upside down), or a mixed one, i.e. with a straight section and a curved one, or else a stepped one with successive shoulders and cylindrical or conical portions whose dimensions decrease toward head 7.

Hereinafter, the term dilator, with or without the reference 1, is meant to designate any dilator according to the invention, regardless of its shape (or contours or perimeter, these terms referring to the shape rather than to the measurements) of the cross-section and/or of the profile of its active portion 4.

Generally, as will easily be understood from the description of the actuation of the dilator, in contrast to the punches of the prior art, the cross-section of the active portion 4 of the latter may have any shape other than circular. By convention, the non-circular character is defined here as the fact that the relative distance between the diameter of the circle passing through the point or the set of points of the cross-section furthest from the rotation axis and the diameter of the circle passing through the point or the set of points of the cross-section nearest to said axis is equal to or greater than 0.5%. The cross-section of the dilator, i.e. of its active portion, is defined according to and results from the combination of the desired shape (or perimeter) of the cross-section of the osseous site, on one hand, and on the other hand, the movement or the combination of movements that are to be applied to the dilator.

According to a first embodiment with many possible variants, the dilator allows to produce holes or implant seats whose cross-section is circular. One advantageous shape of the cross-section of the active portion of the dilator among an infinite number of possibilities is that of a polygon, advantageously convex and regular, or that of a figure having a generally polygonal shape, with or without specific particularities, the angles of attack (see below) preferably being obtuse.

Thus, in a first variant 10 illustrated in FIG. 3, the cross-section (or radial section) of the dilator is hexagonal (by convention, a particular variant will be designated by the same reference as that of the cross-section that represents a particularity thereof). The regular hexagon with contour 12 is inscribed in a circle 11 (fine dashed line). For the sake of simplicity, the six sides and the six apexes carry the same references as the corresponding faces and edges of active portion 4 (FIG. 1), i.e. 13 and 14, respectively (a simplification that will be adopted in the following description of other variants). In a non-represented variant, each one of apexes 14 may be broken, e.g. by forming a slight chamfer by polishing, so as to avoid the risk of a cutting effect (or at least to minimize such risk) of the corresponding edges. Further illustrated in FIG. 3 is an angle α, hereinafter called angle of attack (equal to 120° here) in an imaginary rotation in the direction R1 (clockwise direction). (Note: in this FIG. 3 as well as in the following ones, identical elements are not necessarily always referenced).

Figure 4:
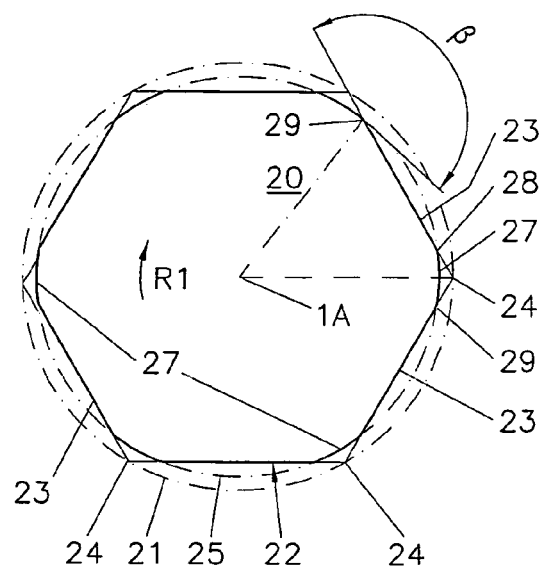

In a second variant illustrated in FIG. 4, which is analogous to variant 10, the perimeter 22 of cross-section 20 (non-hatched) of the active portion of the dilator results from a circle 25 and a regular hexagon (with sides 23 and apexes 24) inscribed in a circle 21 that is concentric to circle 25 (it will be noted that certain particularities of the shape of this variant 20 that are apparent from this figure, as well as those of the following variants that will be described below, are not illustrated in FIG. 2). Thus, instead of being sharp as in variant 10, the six apexes of cross-section 20 are chamfered here, i.e. constituted of circle arcs 27 having ends 28, 29 and extending between sides 23. On account of the small diameter of circle 25 (in practice, the greatest outer diameter in a given set of dilators varies between about 3 and 6 mm), these circle arcs are assimilable to flats whose length is advantageously of the order of one to three tenths of mm. Compared with variant 10, this construction reduces the (aforementioned) cutting effect of a sharp edge of the polygon and increases the angle of attack β (angle of the apex formed at each end 29 and whose two sides are side 23 and the tangent to circle 25 at point 29) (β>α, rotation in the direction of arrow R1).

Cross-section 30 (nonhatched) illustrated in FIG. 5 constitutes a third variant that is analogous to variant 20 of FIG. 4 except for a particularity of its shape that will be explained below. An initial contour 32 results from a regular hexagon inscribed in a circle 31, with sides 33 and apexes 34, and from a circle 35 that is concentric to circle 31, thereby obtaining six chamfered apexes that are constituted of circle arcs 37 with ends 38, 39 extending between sides 33). Based on this fundamental cross-section, sides 33 are incurved towards the axis of the dilator to form concave sides 33A, e.g. by machining of the respective faces of active portion 4 according to a defined radius of curvature ρ. A contour 32A is thus formed of six concave sides 33A that are separated by rounded apexes 37A, the latter being again assimilable to flats with ends 38A, 39A. This perimeter is similar to a modified hypocycloid with six sides and six rounded apexes. The angle of attack at apex 39A (rotation in the direction of arrow R1) is designated by γ (angle formed at each apex 39A, the sides being constituted by tangents to circle 35 at 39A and to the circle with radius ρ). It is observed that at each apex, the length of circle arc 37A is substantially smaller than that of circle arc 37, this reduction being of course a function of the value chosen for curvature radius ρ.

Figure 5:
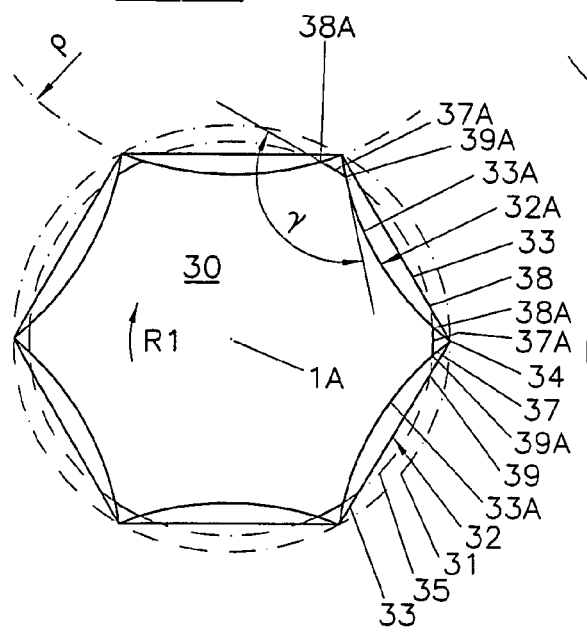

A fourth variant (nonhatched cross-section 40) illustrated in FIG. 6 is analogous to variant 30 of FIG. 5, except that the near hypocycloidal perimeter (designated here by 42B) is modified, one of the sides (reference 43B) being provided with an incision 50, thereby forming with one of the ends 48A of a circle arc or flat portion 47A (ends 48A, 49A) a pointed apex 51 forming on active portion 4 a cutting edge having an angle of attack δ in the rotational direction indicated by arrow R2, the angle of attack γ at points 49A (see also FIG. 5) remaining the same. Of course, it is possible to provide a plurality of cutting edges, and a plurality of sides 43B, or even all of them, may be shaped such that a plurality of apexes comprise a point 51. This variant offers the advantage that the practitioner need not change tools in the course of an osseous compression procedure, as will be explained herebelow in the section relating to the devices for the operation of the dilator.

It is understood that a large number of other sectional shapes may be realized. More particularly, the initial polygon might be a pentagon, an octagon, etc., whereas the sides may have particular designs.

By way of example, FIG. 7 illustrates a cross-section 55 of a generally hexagonal shape whose sides 56 correspond to a kind of sinusoid and all apexes 57 of which (i.e. all corresponding edges) offer the advantage of providing a twofold condensing and cutting function (see below).

According to another embodiment, also with numerous possible variants, the dilator is designed such as to produce an implant seat whose cross-section reproduces or at least approximately approaches the cross-section of a natural alveolus that deviates substantially from the circular shape (see FIG. 1).

FIG. 8 shows a dilator 1 with a cross-section 60 (honhatched) and symmetrical axis 61, comprising a circular main portion 62 and at least one protuberance (the shape being approximately that of a cam), in the illustrated example two protuberances 63, 64 that are symmetrical with respect to axis 1A (approximately the shape of a double ovoid). These protuberances with curved flanks comprise ends 65, 66 (that may be chamfered by grinding). By an adequate actuation of the dilator, as will be seen in the following, an implant site with a perimeter 67 is obtained which roughly corresponds to a Cassini's curve and approaches the contour of a natural alveolus according to FIG. 1H. Based on this example, it is easily understood that other sectional shapes may be realized for shaping an implant bed whose perimeter reproduces or at least optimally approaches the perimeter of a natural, non-circular alveolus (e.g. a cross-section the shape of a simple ovoid). These dilators with specific cross-sections (of which sets of increasing dimensions may be provided too) are advantageously applied, as the case may be, after a first elaboration of a circular hole by means of dilators according to the first embodiment (FIGS. 3 to 7).

Now the operating mode of the dilators of the invention for shaping an implant site will be explained.

As mentioned earlier, after a possible elaboration, in a first phase, of a pilot hole of small diameter (e.g. 2.0 mm) and a desired depth P by usual drilling, the implant site is progressively dilated by means of a set of dilators of increasing dimensions until the elaboration of the final osseous seat intended for the placement of the implant is completed, the increment being generally of the order of 0.10 to 0.25 mm, while it is understood that the practitioner will adapt the latter to the momentary circumstances (e.g. choice of a smaller increment in the case of hard bone or when approaching the final diameter intended for the seat).

Each dilator 1 of a set is subjected to two types of movements, namely a translational movement along axis 1A and a rotational movement in the clockwise and/or counterclockwise direction.

According to one procedure, these two types of movements, translation and rotation, are effected in two successive phases to accomplish the compression of the osseous wall.

A first phase consists in the axial introduction of a dilator 1 into the hole by repeated axial strokes transmitted to stem 2 until a defined depth is attained (which may be equal or inferior to the final depth P of the implant seat, which may be attained little by little). This first phase entails a first, very limited compression of the osseous matter. As will be appreciated by reference to FIGS. 9 and 10, compared to traditional circular dilators, the introduction of a dilator according to the invention is gentle as the amount of displaced/compressed matter is considerably reduced. Actually, to enlarge the implant seat from a diameter D1 to a diameter D2 by means of the traditional method using cylindrical punches, the amount or volume of osseous matter that has to be compressed by a punch having a diameter D2 corresponds to the hatched area 70 multiplied by the momentarily chosen depth P of the hole, by means of necessarily highly intense axial strokes. In comparison (see FIG. 10), the amount or volume of osseous matter to be compressed during the axial introduction of a dilator according to variant 30, for example, corresponds to the sum of areas 71 multiplied by the same depth, which is much smaller than area 70. The discomfort caused in a patient by the osseous preparation of the implant seat is thus extremely reduced. On the other hand, the axial advance of the dilator is perfectly and easily controllable by the practitioner.

A second phase consists in applying to the same dilator a rotation in a direction R1 (indicated in FIGS. 3-8 and 10). Nearly the entire condensing operation takes place in this phase, the dilator dislocating and simultaneously condensing the osseous matter toward the periphery, the meshes of the latter being gently compressed without any removal of osseous portions. In FIG. 10, the amount of compressed osseous matter corresponds to the sum of the areas 72 multiplied by the depth P (or the momentary depth) of the hole. This phase of the compression causes no discomfort for the patient as it carried out without strokes on the dilator. The angular width of the rotation or the number of turns of the dilator are decided case by case by the practitioner, the minimum angle being primarily dictated by the choice of the active cross-section of the dilator (thus, referring e.g. to variant 10, the practitioner will turn the dilator over an angle of 60° at least to obtain the circular shape of the implant seat), and/or by the cross-section that is intended for the osseous site.

Thus, referring to FIG. 8, the compression of the osseous wall of the hole not only results from the rotation in the clockwise direction R1 but also from oscillating movements effected over an angle ω in the directions R1 and R2. Thus, with the aforementioned cross-section 60 of the tool, the implant seat with perimeter 67 is obtained which is similar to the shape of a natural alveolus according to FIG. 2H.

Besides the resulting compression of the osseous matter, the rotational movement allows a fine adaptation of the compression to the (variable) quality of the bone and thus provides control over the calibration of the seat. In particular, if the bone is spongy, the practitioner will limit the rotation to a minimum, whereas if the bone is hard, and thus also more elastic, he may decide to impart the dilator a turn or even several complete turns, thereby optimizing the quality of the wall of the osseous site and simultaneously facilitating the extraction of the dilator from the seat.

If the dilator comprises at least one cutting edge (see FIGS. 6 and 7, edges 51 and 57 respectively), a rotational actuation in the counterclockwise direction R2 will result in a cutting function. Such rotation may be limited in amplitude or effected over one or several turns. Furthermore, it may or may not be accompanied by a translational movement. The application of a dilator combining the functions of condensing the osseous wall and of cutting may be useful particularly if an advance of the dilator in the axial direction encounters difficulties, due for example to the presence of denser osseous zones than traversed beforehand during the insertion of the dilator toward the bottom of the osseous site, or if a difference in osseous density tends to deviate the dilator from the correct working axis (due to the presence of an osseous cortex of asymmetrical thickness, for example, as it is frequently encountered in the elaboration of sites for the superior incisors and canines).

In another procedure, the two types of movements, translation and rotation, are effected concomitantly for achieving the compression of the osseous wall.

It is understood that in this case, the edges of the dilator are preferably at least slightly helical instead of being straight as represented in FIG. 2. This will facilitate the penetration of the tool into the hole as it is subject to a tractive force that tends to advance it towards the interior of the osseous site. In fact, the condensing action resulting in the first phase of the first procedure (that may be qualified as auxiliary compression, see above), and the accompanying axial strokes, even though their impulse is negligible as compared to that created by the tools of the prior art, is completely eliminated. In other words, it is as if the two phases of the first procedure were united in a single one, i.e. the "auxiliary" compression, on one hand, and the proper compression that is the result of the rotation alone, on the other hand, take place at the same time. Also, a possibly remaining discomfort due to the mentioned strokes is totally annihilated.

Finally, regarding the apical portion or impact head 7; 7' (see FIGS. 2A and 2B), the latter may be configured to or inversely not to exert a cutting action, all combinations (four in number) being possible: cutting action only upon rotation R1; cutting action only upon rotation R2; cutting action both upon rotation R1 and rotation R2; no cutting action neither upon rotation R1 nor upon rotation R2.

It is understood that in an alternative embodiment of the described examples, the action exerted by the active portion of the dilator according to the rotational direction might be inverted so that a rotation in the direction R1 results in a cutting action if the tool comprises at least one cutting edge (or a compression in the absence of such edge) and a rotation in the direction R2 causes a compression. This inversion is applicable in analogy to the apical portion.

Regarding the choice of the actual cross-section of the dilator, it is subject to the weighting of different parameters: particularly the intensity of the axial strokes required for the axial penetration of the dilator into the hole (if the first explained procedure is being applied), the risk of tearing off osseous matter, the angle of attack, the amount of osseous matter to be compressed during the axial advance of the dilator. Thus, the axial penetration and the subsequent rotation of the dilator are easier to perform with a dilator according to variant 10 than with a dilator according to variant 20, the surface area and the volume of the displaced osseous matter being smaller in the case of edges 13 than in the case of flats 27. Conversely, the risk of an involuntary removal of osseous matter, especially during the axial introduction of the dilator, may be slightly greater with a dilator of cross-section 10 than with a dilator of cross-section 20. The near hypocycloidal shape of cross-sections 30 and 40 allows to overcome the drawback mentioned with regard to cross-section 20 in that the amount of osseous matter to be compressed in the axial movement is further reduced while the angle of attack remains relatively large. This is why a cross-section of the type represented in FIGS. 5 and 6 constitutes a very satisfying compromise: substantial reduction of the intensity of the axial blows and excellent control over the adjustment of the compression of the osseous matter during the rotation of the dilator (direction R1). These considerations also apply at least partially when the second described procedure is being applied.

Since defined movements have to be imparted to the dilator for producing a defined implant seat, the specialist is confronted with the problem regarding the means for accomplishing those movements. This is the object of the second aspect of the invention, which refers to novel devices some embodiments of which will now be described by way of non-limiting examples while the devices may be roughly classified into two categories, the first one relating to automatic devices, and another one to manual devices.

To start with the first mentioned category, an advantageous embodiment of an automatic device 100 is represented in a perspective view in FIG. 10 and in a sectional view according to a plane of symmetry P (FIG. 10) passing through axis 1A that coincides with the axis of the same reference of dilator 1 in FIG. 11. FIGS. 12, 13, and 14 show the different essential components shown in FIG. 11 on a greater scale.

Device 100 is in the well-known general form of a contra-angle head 101 situated in the prolongation of a handle 102 and in which a dilator is inserted, more particularly a dilator 1 according to the invention. The head comprises a housing 103 accommodating, in two chambers 104A (lower chamber), 104B (upper chamber) that are separated by a dividing wall 104 with a central, non-referenced opening, a mechanism that ensures particularly the functions of a chuck, i.e. the attachment and actuation of the dilator, at least one element of the mechanism being subject to the action of a transmission shaft 118 at the end of which a pinion 119 is fastened.

The mechanism allows the actuation of dilator 1 both translationally, i.e. axially, and rotationally in the clockwise and counterclockwise directions. To this end, according to one example of a translational means, it is essentially provided with a striker 130 that is arranged on top of a rotational driving member 120. These two elements 120, 130 cooperate with each other and form a passage 120A, 130A for receiving the dilator 1.

The dilator 1 inserted in passage 120A, 130A is fastened to striker 130 and detachable therefrom by a classic locking/ unlocking system of the prior art including an uncoupling knob 105 with an attached tongue (not shown) under the action of an uncoupling spring 106, a latch 107 provided with a projection 107A, and a latch retaining spring 108 accommodated in a groove 148 of striker 130 (FIG. 12) and surrounding the latter together with latch 107. To lock it, the dilator is inserted in passage 120A, 130A while simultaneously pressing on uncoupling knob 105 against the force of spring 106, the above-mentioned tab thereby disengaging latch 107 towards the rear of the prolongation of passage 103A with respect to axis 1A. When the shoulder 3A of head 3 of the dilator abuts to a heel 142 of striker 130, the pressure on knob 105 is released and latch 107 enters into groove 3B of dilator 1 under the action of retaining spring 108 to lock the dilator. Unlocking of the dilator 1 is achieved by the inverse operation, a pressure on knob 105 resulting in the disengagement of latch 107 from groove 3B of dilator 1 and thereby liberating it.

Rotational driving member 120 with bore 120A is formed of a reducer that is accommodated in lower chamber 104A and simultaneously serves as a freely rotatable step bearing. Reducer 120 comprises a conical toothed crown 127 meshing with pinion 119, the reducer demultiplying the rotational speed of transmission shaft 118 and thus multiplying the torque that is transmitted to striker 130. The lower portion of reducer 120 comprises a guiding journal 128 that is guided in a bearing 129. Above crown 127 extends a surface 126 that provides a sufficient clearance for pinion 119 and opens to form a collar 125. The upper face of the latter comprises a shoulder 124 resting on dividing wall 104 e.g. via a revolving joint (not shown), and a helical ramp 121 originating after a flat 123, in the present example over 360° (including flat 123), the end portion of the ramp forming a bearing surface 122.

Translational driving member 130 (in the present case the striker) with bore 130A is formed of a stepped cylindrical piece accommodated in upper chamber 104B. The lower portion of member 130 comprises a ramp 131 that cooperates with ramp 121 of the reducer and whose shape is complementary to the latter (helical slope originating after a flat 133, angle of 360° (including flat 133, the end portion forming a bearing surface 132). Above ramp 131 extend a central portion 134, a collar 141 that is separated from central portion 134 by a groove 140, and an end portion 145 extending upwards from the upper face 143 of collar 141. Central portion 134 comprises two guiding openings in the form of straight, diametrally opposed slots 135 whose height is at least equal to twice the height of bearing surface 122 of the reducer (or 133 of the striker) and whose respective left-hand flanks 136 are chamfered. At the height of collar 141, a heel 142 forming a stop for shoulder 3A of the dilator enters into passage 130A. End portion 145 comprises an opening 146 in which the latch of dilator 107 may enter, as well as a groove 148 in which retaining spring 108 is seated.

An elastic member 109 is arranged around portion 145, more particularly spring washers or Belleville springs whose lower and upper edges (not referenced) rest on upper face 143 of collar 141 and on a cap (not referenced) of housing 103, respectively. Elastic member 109, working by compression (i.e. exerting a force that is opposed to a compressive force acting thereon) constantly presses the striker against reducer 120.

One end 116 of a selector arm 115 may be engaged indifferently in one or the other one of slots 135 or disengaged from these openings by actuating a selector knob 117. Arm 115 is arranged such that a slide 110 to which it is connected through a pin 114 is positioned at the height of groove 140 of the striker when the latter is the lowered position (see below).

The slide is provided with opposed inner and outer protuberances 111 and 112, respectively, inner protuberance 111 being adapted to engage in groove 140 and outer protuberance 112 in a groove 113 arranged in the housing.

The operation of device 100 is as follows: When transmission shaft 118 is actuated, its rotational movement is transformed in such a manner that dilator 1 may be driven translationally, i.e. axially, by subjecting the latter to reciprocating movements in axis 1A, or rotationally.

In the example, the translational movement is accompanied by a percussion effect on dilator 1. To achieve this effect, end 116 of the selector arm is engaged in one of slots 135, thereby blocking the extent of the rotational liberty of striker 130. Transmission shaft 118 rotationally drives reducer 130 in the direction indicated by arrow R1 (clockwise direction). Assuming a starting point where flat 133 of ramp 131 of striker 130 rests on flat 123 of ramp 121 of reducer 120 while the respective faces 132, 122 face each other (lowered position of striker 130, approximately corresponding to the position represented in FIG. 9), striker 130 is progressively pushed upwards against the action of elastic member 109 until a complete turn is accomplished (lifted position of striker 130), an then is driven towards reducer 120 by elastic member 109 the sudden liberation of whose stored energy produces a percussion that is transmitted to dilator 1 connected to striker 130, the latter now having returned to the aforementioned starting point where flats 133 and 123 are again applied to each other. The practitioner repeats these percussion cycles while dilator 1 progressively penetrates into the implant bed and simultaneously condenses the osseous matter until dilator 1 has attained the defined depth P of the implant seat. It is understood that the practitioner may adjust the axial pressure of the dilator in the implant seat at will by exerting an axial force (in the direction of axis 1A) in one or the other direction.

To accomplish the second step in which the osseous matter is compressed (referring more particularly to the first one of the two procedures described above with regard to the types of movements imparted to the dilator), the practitioner will now bring about a rotation of dilator 1—whose angular width he may determine—only in the clockwise direction R1 or alternatively both in the clockwise direction R1 and in the counterclockwise direction R2, depending on the type of dilator (see above) that is being used. To this end, the practitioner disengages end 116 of selector shaft 115 from slot 135 by pulling selector knob 117 backwards, thereby conferring striker 130 the ability to rotate. At the same time, slide 110, i.e. protuberance 111 of the latter, engages in groove 140 of striker 130, thereby restraining the extent of translational liberty of striker 130 (or extent of liberty of axial movement). Striker 130, in the lowered position, is rotationally driven by the reducer against which it is being applied by elastic member 109.

If the practitioner decides in the course of the osseous preparation that in a given location it would be advantageous, e.g. for carrying out a momentary or more extended cutting (or scraping) operation, or for overcoming a resistance due to a hardness of the bone that may be local or extend over a greater distance, and assuming, of course, that the dilator currently attached to striker 130 is of the type comprising a cutting edge (see variant 40 of the first embodiment of dilator 1), the practitioner will cause the dilator to rotate in the counterclockwise direction R2 over an angle that he may determine and which will often amount to a few degrees only but might be substantially greater and even exceed 360°. To this end, he will simply reverse the rotational direction from R1 to R2 (see preceding paragraph) without the need of changing tools, i.e. without making use of a conventional cutting tool.

The described embodiment comprises a safety system in that when a rotation in the direction R2 is requested (reversal of the rotational direction of transmission shaft 118), end 116 of selector shaft 115 is automatically disengaged from slot 135 due to the rounded or expanding shape of left-hand lateral flank 136 of slot 135, on which said end is resting. Moreover, in this counterclockwise direction, bearing surface 122 of the reducer is being pushed against bearing surface 132 of the reducer, thereby preventing any sliding movement of the striker, considering that the torque required for the punctual cutting operation is greater than that required for the osseous compression operation.

It is apparent to those skilled in the art from this embodiment that the two movements may be combined, in which case the dilator is simultaneously subject to a translational movement and to a rotational movement in any of the two directions in conformity with the second one of the two procedures described above with regard to the types of movements that are imparted to the dilator. Thus, for example, dilator 1 may be subject, concomitantly to the translational movement which in turn is accompanied by a percussion, to a rotational movement over a limited angle in one direction or another due to a helical configuration of slots 135, the helix possibly having a right-hand or left-hand pitch instead of being straight.

Thus, device 100 offers an additional advantage of high interest, namely its polyvalence: Beyond the privileged application in the preparation of implant seats that has just been discussed, this device actually allows performing all traditional forms of drilling.

By way of examples, two embodiments of less sophisticated embodiments belonging to the second mentioned category (manual devices) will now be described with reference to FIGS. 15 to 19 (first exemplary embodiment) and 20 to 22 (second exemplary embodiment).

Device 200 (FIG. 15) includes a handle 201 with main axis 201A that is composed of a front portion 202 and a rear portion 203, a head 204 for the attachment of a dilator 1 with main axis 1A, arranged at the front end of portion 202 of handle 201, and of a percussion device 205 arranged in the rear area of portion 203 of handle 201 and cooperating with portion 203.

Head 204 (see FIGS. 16 and 17) is a shaped piece 206 comprising a heel 207 at its front end and an opening 208 having an axis 1A in which the stem 2 of dilator 1 (FIG. 1) is attachable or from which it is detachable, the upper part of opening 208 being partially obturated by a stop 209. In the prolongation of axis 201A, the rear end of piece 206 is provided with an opening (not referenced) in which a fastening member 210 is seated which connects head 204 to handle 201. Between the two aforementioned openings, a third opening (not referenced) is arranged in which a pivot 211 with axis 211A is mounted on which a latch 212 arranged on the upper face (not referenced) of piece 206 may pivot, said latch having the form of a small, approximately triangular plate with strongly rounded edges. In front of pivot axis 211A, the latch is provided with two overlapping openings 213, 214 (whose non-referenced axes are parallel to axis 1A), the diameter of opening 213 corresponding to the diameter 3B of the groove in the stem of dilator 1 (for references 3A, 3B, 3C, 3D, see FIG. 1), and the diameter of opening 214 corresponding to the diameter of cap 3D. Latch 212 allows locking dilator 1 to head 204 translationally when engaged in groove 3B of the dilator after having introduced the latter until shoulder 3A contacts stop portion 209, flat 3C opposite said stop locking the dilator rotationally (position shown in FIG. 16).

Percussion device 205 (FIGS. 18 and 19) comprises a weight 215 capable of sliding along portion 203 of shaft 201 while preferably being rotationally locked by an element 216 whose end (not shown) is guided in a groove 217 of portion 203. The weight can be fixed at the end of portion 203 by a catch 220 arranged on the upper face thereof (not referenced), the catch pivoting around a pivot 221 upon manual actuation of a knob 222 and being movable toward a groove 218 arranged in the upper portion of element 203 of handle 201 (FIG. 19, catch 220 in the lowered position). Finally, the percussion device comprises a knob 226 fastened to the upper face (not referenced) of portion 203 of handle 201 by a fastening member 227.

To achieve the axial insertion of the dilator into the implant seat, the practitioner releases weight 215 by opening catch 220 and strikes it against a shoulder 225 (FIG. 18) arranged in the upper section of portion 202 of handle 201. When the dilator has reached the intended depth, the practitioner proceeds to the osseous compression by rotating device 200 manually. Of course, it is also possible to impart the dilator a rotational movement simultaneously to the percussion. To extract the dilator from the implant seat, the practitioner may strike weight 215 against knob 226, if necessary.

The device may be realized with handles 201 of different lengths (e.g. a set of handle portions 202 of different lengths, or by providing a telescopic element 202) to ensure a good accessibility in all circumstances. On the other hand, it is obvious that a fastening head might be designed in such a manner that axis 1A of dilator 1 and axis 201A of handle 201 coincide.

Device 300 illustrated in FIGS. 20, 21 and 22 is composed of a handle 301 with main axis 301A (almost identical to handle 201 as described above) that is fastened to an arm 303 with main axis 303A to one end of which a contra-angle head 302 (known per se) is mounted which holds dilator 1 with axis 1A, the other end being provided with a wheel or thumb wheel 304. In the example, axes 1A, 301A and 303A extend in the same plane and axes 1A and 301A are parallel to each other.

Dilator 1 is translationally locked by a locking system 211, 212 of the same kind as described with regard to device 200. However, in contrast to the latter, the dilator can be rotationally driven by a mechanism that is accommodated in a casing 305 of head 302 (see FIG. 22 where this mechanism is visible, head 302 being represented without the casing). This mechanism comprises a drive sleeve 306 inside which a stop cooperates with shoulder 3A and flat 3C of the dilator (said stop, shoulder 3A and flat 3C not being visible in the Figures, taking into account that those skilled in the art, knowing this mechanism, may conceive other constructive elements of any kind for ensuring the connection between the dilator and the sleeve). Sleeve 306 is provided with a toothed crown 307 meshing with a spur pinion 308 forming the end portion of a shaft 309 that is guided in a tube 310 of arm 303. Thumb wheel 304 is fastened to the end opposite shaft 309 by means of a non-represented fastening member.

A block 312 is slidable along tube 310 and may be fastened on the latter in a defined position by means of a set screw 313 according to the conditions regarding the accessibility of the implant bed in the patient's mouth. In order to preserve an unrestrained rotation of block 312, and more particularly the parallelism between axis 301A and axis 1A of the dilator, tube 310 of arm 303 comprises a flat portion 311 on which the set screw is resting. Handle 301 is fastened to the block on the upper face (not referenced) thereof, e.g. by a screw connection.

After exerting the translational movement by actuation of percussion device 205 (see FIG. 21 and the explanations given above in the context of device 200), the rotational movement of the dilator—while it is understood that device 300 allows a rotation in the clockwise and counterclockwise directions (condensing and scraping or cutting action, respectively)—is effected by an actuation of wheel 304 (in most cases, the number of turns performed with the dilator is equal to two at the most and will often be smaller than one). As with device 200, while being subject to a translation along axis 1A, the dilator may simultaneously be rotated around this same axis.

It is understood that many other embodiments or variants of manual or automatic devices might be conceived without leaving the scope of the present invention. It will be noted in this context that beyond the rational aspect provided by the possibility of detaching the dilator, regardless of its type, from the device for its operation, the fact that the handles of the manual devices comprise a system for a translational actuation, advantageously by means of a striker including a weight, as well as the automatic generation of axial strokes (automatic device), means that have been inexistent in the past, particularly allows an improved control over the calibration of an implant seat even if conventional cylindrical dilators (punches) are used, but all the more when the precedently described and claimed dilators are being used. Furthermore, the application of such devices may extend beyond the mere preparation of osseous seats. In particular, they appear to be perfectly appropriate for receiving tools for performing maxillary sinus elevation surgery (by the technique of elevating an alveolar bone fragment).

The osseous preparation tools and the devices for their operation according to the invention form the two pillars of a highly innovative integrated system—rightly called "SDS" ("soft dilating system")—that contributes its part to a considerable extension of the fields of application of implantology.

The invention claimed is:

1. Osseous compression tool for use particularly in dentistry for the preparation of an osseous seat in view of the placement of an axially inserted implant, the tool comprising an active portion that allows shaping said osseous seat and may be terminated by an apical portion, characterized in that the cross-sectional shape of the active portion is defined such that a rotational movement of the tool around an axis has the effect that the osseous matter is compressed towards the periphery of the seat and that the latter is simultaneously imparted a determined shape, while its angular width is essentially determined by the respective type of contour of the cross-section of the tool and by the mechanical qualities of the worked osseous matter, and in that it may be oriented in the clockwise or in the counterclockwise direction or reciprocating in one and in the opposite direction, and in that said cross-sectional shape is other than circular, the non-circular character being defined as the fact that the relative distance between the diameter of the circle passing through the point or the set of points of the cross-section furthest from the rotation axis and the diameter of the circle passing through the point or the set of points of the cross-section nearest to said axis is equal to or greater than 0.5%.

2. Tool according to claim 1, characterized in that said defined cross-sectional shape of the active portion is determined according to the predetermined shape of the osseous seat, on one hand, and according to the movement or the combination of movements imparted to the tool, on the other hand.

3. Tool according to claim 1, characterized in that said cross-sectional shape is at least approximately asteroid or petaloid with at least three branches.

4. Tool according to claim 1, characterized in that said cross-section comprises at least one eccentric portion.

5. Tool according to claim 1, characterized in that said cross-sectional shape is approximately ovoid with an apex that is preferably rounded or in the shape of a circle segment.

6. Tool according to claim 1, characterized in that said cross-sectional shape is approximately that of a double ovoid with two opposite apexes that are preferably rounded or in the shape of circle segments.

7. Tool according to claim 1, characterized in that its rotational actuation may be bi-directional and/or angularly limited.

8. Tool according to claim 1, characterized in that in an axial plane, the active portion has a profile that is determined in function of the intended axial profile of the osseous site.

9. Tool according to claim 8, characterized in that the profile of the active portion may be straight, curved or a combination of straight and curved.

10. Tool according to claim 8, characterized in that the profile of the active portion is stepped in a succession of shoulders whose dimensions decrease towards the apical portion.

11. Tool according to claim 1, characterized in that the active portion comprises at least one edge and in that this edge is straight or helical.

12. Tool according to claim 11, characterized in that at least one edge is sharp, rounded, or in the shape of a flat.

13. Tool according to claim 1, characterized in that the active portion comprises two subsections, a rear subsection being followed by a conical front subsection ending in the apical portion, the conicity preferably being of the order of 1°.

14. Tool according to claim 13, characterized in that the length of the front subsection corresponds to the depth of the implant seat at least approximately.

15. Tool according to claim 7, characterized in that a compression of the osseous wall of the implant seat is produced by the rotation of said tool both in the clockwise and in the counterclockwise directions.

16. Tool according to claim 11, characterized in that its rotation in one direction causes a compression of the osseous wall of the implant seat and its rotation in the opposite direction causes a cutting or scraping of the osseous wall of the implant seat, at lest one edge being a cutting edge.

17. Tool according to claim 8, characterized in that the apical portion may exert a cutting action, either in only one of the two rotational directions or in both rotational directions.

18. Device for the operation of an osseous compression tool according to claim 1, characterized in that it comprises means for imparting to the tool a translational movement in the direction of the axis of said tool as well as a rotational movement, and in that the means transmitting the translational movement is formed of a percussion system comprising a striker that cooperates with a member for transmitting a rotational movement, the tool being connected to the striker.

19. Device according to claim 18, characterized in that means for the cooperation between the striker and the transmission member allow to subject the striker to a reciprocating movement of a defined amplitude and to said rotational movement or to a combination of such movements, the resulting movement being transmitted to the tool.

20. Device according to claim 19, characterized in that the cooperation means are formed of two complementary ramps which face each other and are disposed on the member for the transmission of the rotational movement and on the striker, respectively, the latter being subject to the action of an elastic member.

21. Device according to claim 19, characterized in that it comprises selecting means such that the tool performs the intended movement or combination of movements.

22. Device according to claim 21, characterized in that the selecting means are formed of a selector arm whose end cooperates with at least one opening of the striker, the selector arm being controlled by means of a selecting mechanism in such a manner as to impart the striker the translational movement combined or not combined with the rotational movement.

23. Device according to claim 22, characterized in that the opening comprises a rounded flank that allows an automatic liberation of the end of the selector arm from said opening when the striker is rotated in a given direction.

24. Device according to claim 18, characterized in that a percussion system is disposed on a portion of a handle comprising a shoulder, the tool being engaged in a head at the opposite end of the handle and rotationally and translationally locked.

25. Device according to claim 24, characterized in that the translational lock is ensured by a latch that may pivot around a pivot.

26. Device according to claim 24, characterized in that the percussion system comprises a weight that may slide over a distance along a portion of the handle and strike a shoulder provided on the handle.

27. Device according to claim 26, characterized in that the weight is rotationally locked.

28. Device according to claim 26, characterized in that the end portion of the handle comprises a stop that the weight may strike in order to facilitate the extraction of the tool from a hole.

29. Device according to claim 26, characterized in that the weight can be locked to one end of the handle by means of a locking mechanism.

30. Device according to claims 24, characterized in that it is manually rotatable around the axis of the tool, thereby actuating the latter rotationally.

31. Device according to claim 18, characterized in that a percussion system is disposed on a portion of a handle comprising a shoulder, the handle being connected to an arm one end of which is provided with a head for receiving the tool whose axis extends perpendicularly to the axis of said arm and in parallel to the axis of the handle.

32. Device according to claim 31, characterized in that the percussion system corresponds to that defined in claim 31.

33. Device according to claim 32, characterized in that the handle provided with its percussion system is connected to the arm by a connecting element that is slidable along the arm and may be locked thereon by means of a locking means.

34. Device according to claim 33, characterized in that the connecting element is rotationally locked on the arm such as to maintain the parallelism between the tool axis and the axis of the handle.

35. Device according to claim 34, characterized in that the rotational lock is ensured by a flat provided on the arm, the connecting element being provided with a corresponding flat.

36. Device according to claim 31, characterized in that the tool inserted in the head is translationally locked by means of a catch and is freely rotatable, the tool being fastened to a rotatable sleeve.

37. Device according to claim 36, characterized in that the sleeve is in engagement with a transmission shaft which is actuatable by means of a wheel, thereby allowing the rotational actuation of the tool.

* * * * *